(12) United States Patent
Odagiri et al.

(10) Patent No.: US 6,786,866 B2
(45) Date of Patent: Sep. 7, 2004

(54) PORTABLE DEVICE FOR COLLECTING INFORMATION ABOUT LIVING BODY, AND SYSTEM AND METHOD FOR COLLECTING INFORMATION ABOUT LIVING BODY

(75) Inventors: Hiroshi Odagiri, Chiba (JP); Tomozumi Saruwarati, Chiba (JP); Yoshiharu Yamamoto, Tokyo (JP); Benjamin H. Natelson, New Brunswick, NJ (US)

(73) Assignees: Seiko Instruments Inc., Chiba (JP); University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 10/205,941

(22) Filed: Jul. 26, 2002

(65) Prior Publication Data

US 2003/0187336 A1 Oct. 2, 2003

(51) Int. Cl.$^7$ .................................. A61B 5/00
(52) U.S. Cl. ....................... 600/300; 128/920
(58) Field of Search ................. 600/300–301, 600/531, 544–545, 587, 595, 502, 507, 503; 128/903–905, 920–921; 434/262, 118; 340/573.1; 482/4, 8–9, 901; 705/2–4

(56) References Cited

U.S. PATENT DOCUMENTS

| | | | | |
|---|---|---|---|---|
| 4,418,700 A | * | 12/1983 | Warner | 600/507 |
| 4,566,461 A | * | 1/1986 | Lubell et al. | 482/8 |
| 5,197,489 A | * | 3/1993 | Conlan | 600/595 |
| 5,601,435 A | * | 2/1997 | Quy | 434/262 |
| 5,722,418 A | * | 3/1998 | Bro | 600/300 |
| 6,080,106 A | * | 6/2000 | Lloyd et al. | 600/300 |
| 6,249,809 B1 | * | 6/2001 | Bro | 600/300 |
| 6,290,646 B1 | * | 9/2001 | Cosentino et al. | 600/300 |
| 6,409,662 B1 | * | 6/2002 | Lloyd et al. | 600/300 |
| 6,454,705 B1 | * | 9/2002 | Cosentino et al. | 600/300 |
| 6,478,736 B1 | * | 11/2002 | Mault | 600/300 |
| 6,513,532 B2 | * | 2/2003 | Mault et al. | 600/300 |
| 6,569,094 B2 | * | 5/2003 | Suzuki et al. | 600/300 |

* cited by examiner

Primary Examiner—Mary Beth Jones
Assistant Examiner—Michael Astorino
(74) Attorney, Agent, or Firm—Adams & Wilks (57) ABSTRACT

A portable living body information collection device is arranged to continuously measure living body information in daily life and to efficiently collect relating mental information by timely questioning about health. The device can be worn on a human body. The portable living body information collection device extracts living body information in electrical signal form by a detection circuit and a signal processing circuit, and discretizes the information by a conversion circuit. A control circuit stores the discretized living body information in a storage and displays questions about feelings and mental conditions on a display unit periodically or when a large changes occurs in living body information. The wearer inputs answers by using an input device, and the answers are also recorded as mental information in the storage. Write or read of the living body information and mental information recorded in the storage, and various set values to or from an external personal computer can be performed by means of a communication circuit.

20 Claims, 12 Drawing Sheets

PORTABLE DEVICE FOR COLLECTING INFORMATION ABOUT LIVING BODY, AND SYSTEM AND METHOD FOR COLLECTING INFORMATION ABOUT LIVING BODY

BACKGROUND OF THE INVENTION

1. Field of the Invention

The present invention relates to a portable device for continuously collecting information in time sequence about the living body of a wearer of the device in his or her daily life.

2. Description of the Related Art

It is widely known that living physiological information monitoring device for monitoring the status of living bodies have been used to continuously measure living body information for the purpose of assistance in health care, diagnosis and treatment. For example, step counters capable of counting the number of steps made by a wearer while walking to determine the amount of exercise done by the wearer are in widespread use. In use of such step counters, measurement is continuously performed and measurement data is handled by being totaled; that is, the total number of walking steps in one day is used as an index of health care.

U.S. Pat. No. 5,197,489 discloses an attempt to detect fine bodily movements of a wearer and to use data on detected bodily movements in treatments, etc. According to the specification of this patent, each kind of movement has a particular frequency characteristic. For example, the specific frequency of breathing ranges from 0.2 to 1 Hz; that of heartbeat, from 2 to 3 Hz; that of activities during the night, from 0.2 to 3 Hz; and that of tremors, from 2 to 9 Hz. A frequency signal corresponding to each of these particular movements is extracted by changing a filter constant, quantified and recorded in time sequence.

Conventional living body information monitoring devices enable objective measurements of information on a daily or weekly basis about a living body, e.g., measurements of changes of bodily movements, changes in the amount of activity, heartbeat, body temperature, etc. However, they are incapable of obtaining subjective information, e.g., information from a person about the reason why the person was active, or mental information, e.g., information about a person's feeling when the person was active. Ordinarily, such subjective or mental information (hereinafter referred to collectively as mental information) is obtained by a doctor asking a patient questions about patient's health in consultation or asking the patient to fill in an inquiry form. It is possible to elicit information on the mental condition of a patient by asking the patient some questions in consultation or by using an inquiry form. However, it is very difficult to obtain detailed information by going back to the past and it is impossible to determine variation in mental information in correspondence with variation in living body information obtained. A patient may periodically fill in an inquiry form by always carrying it about with him or her to provide mental information in time sequence. However, such a process is troublesome and there is a possibility of the patient forgetting the inquiry form in his or her daily living. Moreover, the conventional method of separately obtaining living body information and mental information entails a drawback of missing important information since it does not enable timely questioning immediately after a change in living body information has occurred.

SUMMARY OF THE INVENTION

An object of the present invention is to provide a portable living body information collector which is capable of continuously measuring living body information in daily life for the purpose of assistance in health care, diagnosis and treatment, which enables efficient collection of necessary mental information by timely questioning about health, and which can be worn on a human body.

To achieve the above-described object, according to one aspect of the present invention, there is provided a portable device for collecting living body information, the device including a detection circuit for detecting living body information and for outputting a signal representing the detected information, storage means for storing the output signal from the detection circuit and for storing at least one question and an answer to the question, a display unit which displays the question, input means for inputting an answer to the displayed question, and a control circuit which makes the display unit display the question at a suitable time, and which stores, sequentially with respect to time, answers input by the input means. With the device, information of the living body of a wearer wearing the portable information collection device and the mental condition of the wearer obtained through the question can be collected in time sequence to be used for assistance in treatment.

According to another aspect of the present invention, there is provided a method of collecting living body information, the method including the steps of averaging the latter half of 2N of living body information items most recently measured at predetermined intervals sequentially with respect to time, wherein N is an integer of 1 or more, averaging the former half of the 2N living body information items, and making a determination as to whether the difference between the average of the latter half of the 2N living body information items and the average of the former half of the 2N living body information items is larger than a predetermined threshold value, wherein questioning about health is performed if it is determined in the determination step that the difference between the averages is larger than the threshold value. This method enables determination as to whether a user to be treated is awake or asleep, and enables timely questioning when the user is awake. Information obtained in this manner can be used for treatment.

DESCRIPTION OF THE PREFERRED EMBODIMENT

Figure 1A:
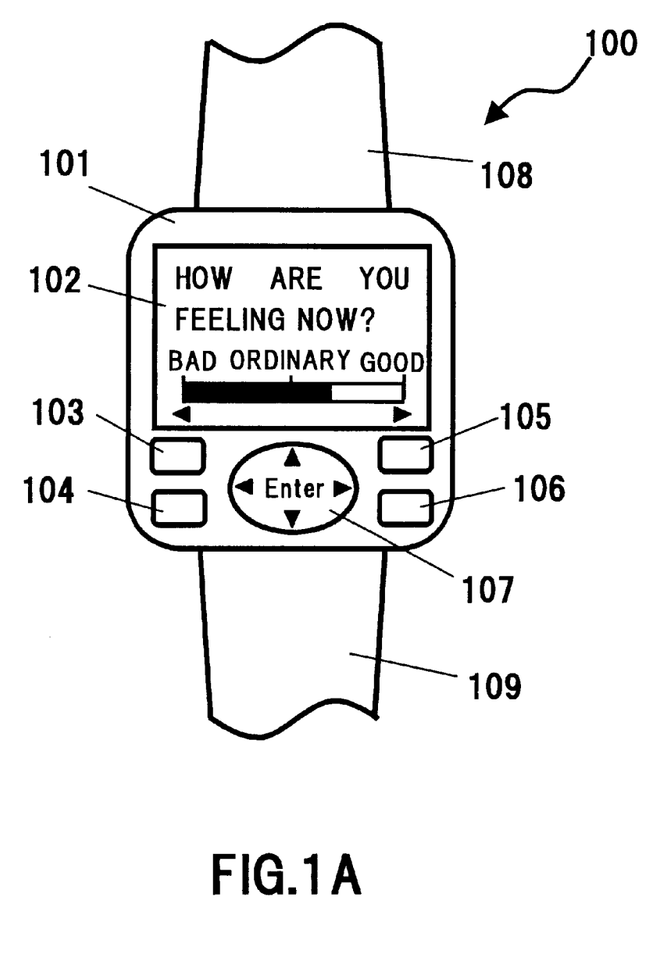
FIGS. 1A and 1B are diagrams showing an external appearance of a portable living body information collector which represents an embodiment of the present invention.
Figure 1B:
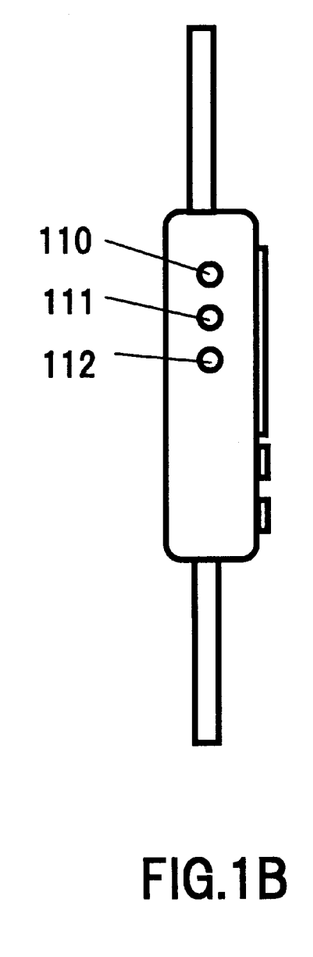

An embodiment of the present invention will be described with reference to the accompanying drawings. FIGS. 1A and 1B are a plan view and a side view, respectively, of an external appearance of a portable living body information collector 100 which represents an embodiment of the present invention. The portable living body information collector 100 is constituted by a main unit 101 and a pair of band members 108 and 109. The portable living body information collector 100 can be worn about a wrist of a wearer with the band members 108 and 109 fitted around the wrist. The main unit 101 has a display 102 and a plurality of keys 103, 104, 105, 106, and 107. The display portion 102, which is, for example, a liquid crystal display (LCD), can be normally used as a wristwatch by being made to display time information. Simple questions such as "How are you feeling?" and "Are you irritated?" are displayed on the display portion 102 at suitable times. The wearer inputs an answer to each question by using the key 107. In this embodiment, the key 107 is an input device of five directions: upward, downward, rightward, leftward, and depressing directions. For example, to answer to the question "How are you feeling?", the wearer inputs the level of feeling at the corresponding time by operating the key 107 in the leftward or rightward direction. In the example shown in FIG. 1, a bar indicator on the display portion 102 changes in length according to the input operation in the leftward or rightward direction, and the input is determined by the depressing operation. The other keys 103, 104, 105, and 106 are used to realize other functions, e.g., a mode change function and a time correction function, which do not directly relate to the present invention and, therefore, will not be described in this specification. Input/output terminals 110, 111, and 112 for connection to an external personal computer or the like are formed in a side surface of the main unit 101.

Figure 2:
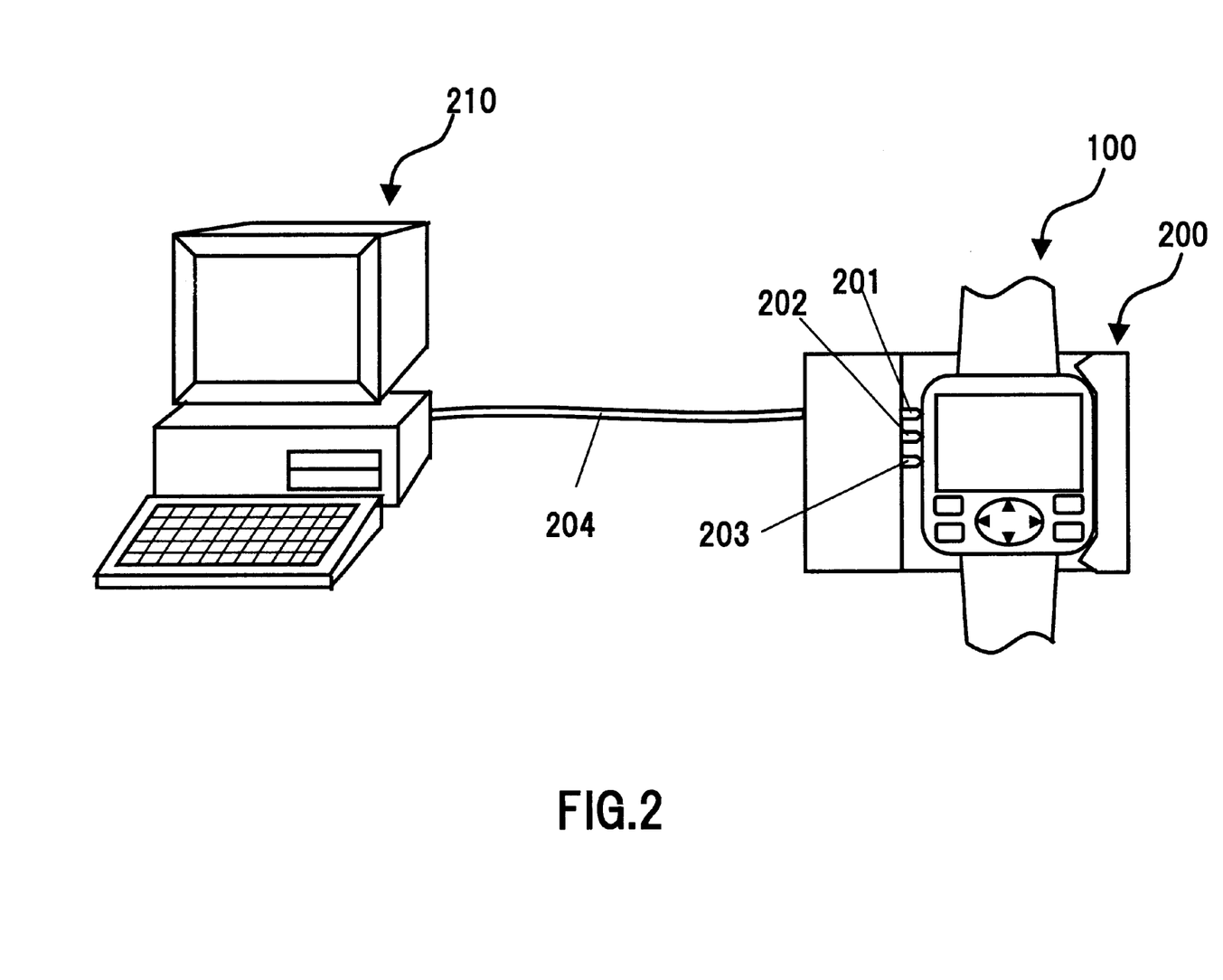
FIG. 2 is a diagram schematically showing a system in which the portable living body information collector of the embodiment and a personal computer are connected to each other and communication is performed therebetween.

FIG. 2 is a diagram schematically showing a system in which communication is performed between the portable living body information collector 100 and a personal computer (hereinafter referred to as "PC") 210 connected to each other. The portable living body information collector 100 is connected to the PC 210 through a docking station 200. Connection pins 201, 202, and 203 are provided on the docking station 200. The connection pins 201, 202, and 203 can be brought into contact with the input/output terminals 110, 111, and 112, respectively, and are connected to an input/output port of the PC 210 by a cable 204. Various set data items and inquiry items for detection of living body information can be easily written from the PC 210 to the portable living body information collector 100 by performing communication between the portable living body information collector 100 and the PC 210. Examples of the set data items are a living body information detection cycle Ts, a detection sensitivity, a questioning cycle Tm, a threshold level C for recognition of change in living body information at which questioning is to be started, and an averaging coefficient N. A threshold value S for skipping of questioning is also set. For questioning, a plurality of questions to be asked may be prepared in advance and a program on the PC may be formed so as to enable selection from the prepared questions, thereby facilitating preparation of a question form. Needless to say, if there is no necessary question in prepared alternatives, a suitable question may be newly made. Conversely, after measurement, living body information obtained by measurement and questioning results are read from the portable living body information collector 100 to the PC 210. The read living body information and questioning results can be processed on the PC 210.

While the docking station 200 and the cable 204 are used for connection between the PC 210 and the portable living body information collector 100 in the described system, a communication means such as an infrared device may be used instead of the docking station and the cable.

Figure 3:
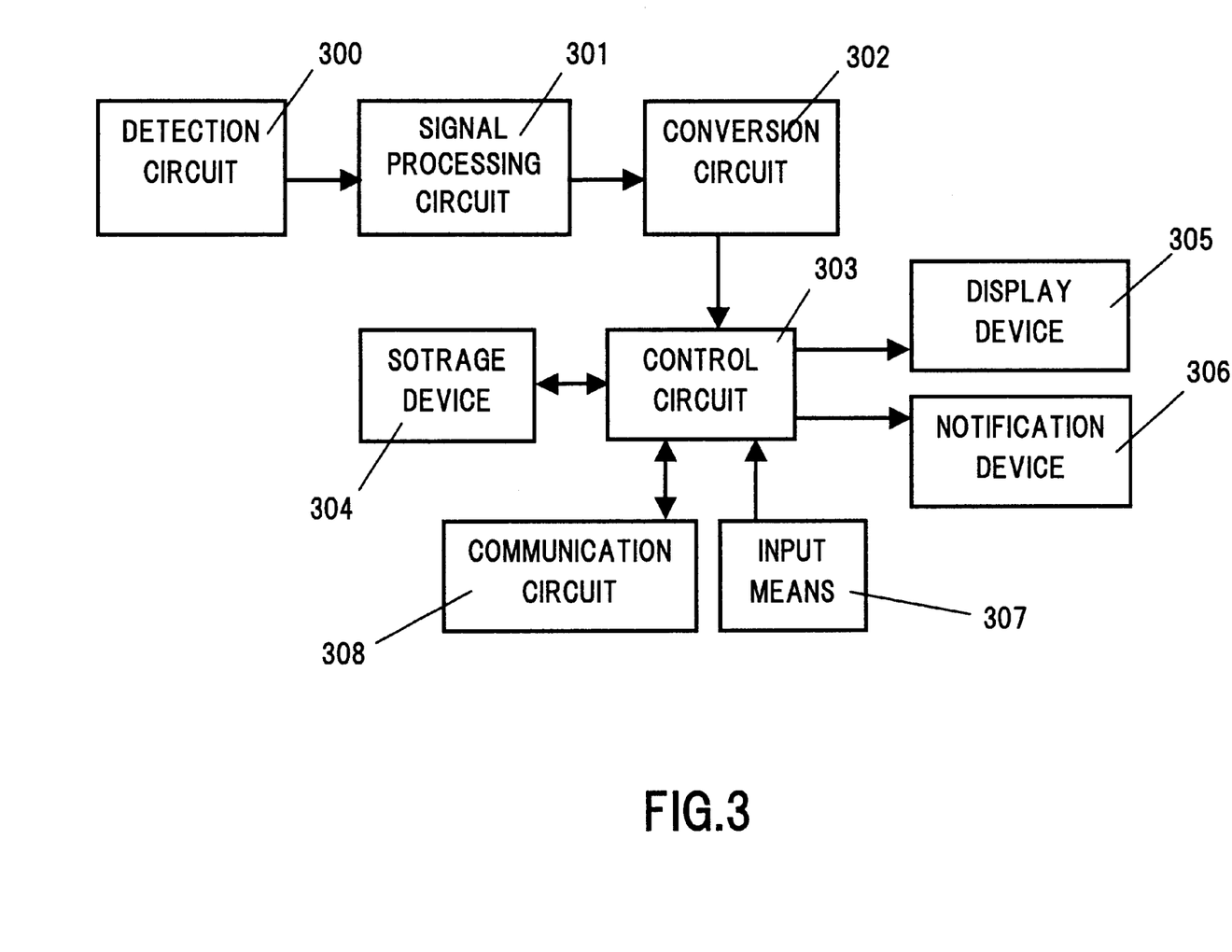
FIG. 3 is a diagram schematically showing the configuration of the portable living body information collector in the embodiment of the present invention.

FIG. 3 is a diagram showing the configuration of the portable living body information collector 100. A detection circuit 300 detects living body information from a sensor and converts it into an electrical signal. The signal output from the detection circuit 300 is faint and contains a substantial amount of noise. Therefore, amplification and filtering are performed on the signal by a signal processing circuit 301. The processed signal is quantified by a conversion circuit 302. The quantification cycle, i.e., the detection cycle is regulated by a control circuit 303 and quantified living body information in each cycle is successively taken into the control circuit. The control circuit 303 records the successively-taken living body information in a storage device 304. The control circuit 303 also performs questioning in a predetermined cycle. At a time when questioning is to be performed, the control circuit 303 drives a notification means 306 to notify the wearer of a start of questioning and shows on a display device 305 a message for notifying the start of questioning, e.g., "Questioning will be started. Are you ready?". The wearer inputs, by means of an input device 307, an answer to the question shown in the display device 305. The input answer is recorded in the storage device 304 by the control circuit 303. The living body information and the result of questioning recorded in the storage device 304 are transmitted to an external PC or the like by a communication circuit 308. The living body information detection cycle and the questioning cycle are also set through the communication circuit 308.

Figure 4:
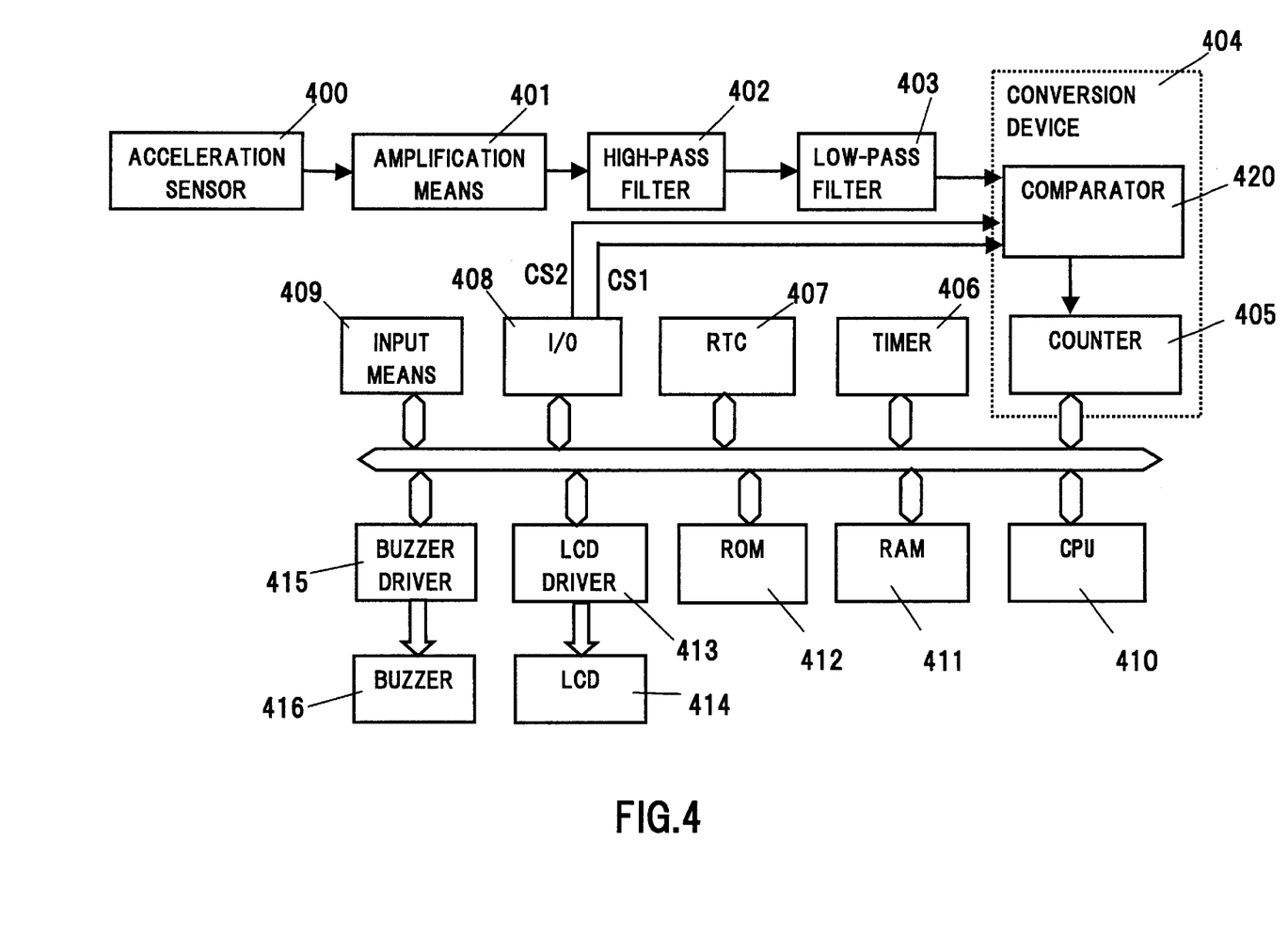
FIG. 4 is a block diagram showing the configuration of the portable living body information collector in the embodiment of the present invention.

FIG. 4 is a block diagram of this embodiment in a case where bodily movements are detected. An acceleration sensor 400 is a piezoelectric-type acceleration sensor having a piezoelectric element made of lithium niobate, lead ziconate-titanate or the like and formed as a cantilever. The piezoelectric element bends by acceleration to generate electric charge. That is, the acceleration sensor 400 detects acceleration according to a movement of the wearer to output a signal, which is amplified by an amplification means 401. Since the amplified signal includes noises and high-frequency components, only necessary frequency components are extracted from the signal by a high-pass filter 402 and a low-pass filter 403. Since the frequency of movements of a human body ranges generally from 0.2 to 9 Hz, the constants of the high-pass filter 402 and the low-pass filter 403 may be selected to extract components in this frequency range. The signal extracted by the high-pass filter 402 and the low-pass filter 403 and representing bodily movements of the wearer is quantified and converted into numeric values by a conversion device 404. To convert the signal representing bodily movements into a numeric value, a method of direct A/D conversion of the signal or a method of digitizing by comparison with a reference voltage may be used. The latter method is more preferable in terms of reduction in size and in power consumption. In this embodiment, therefore, the conversion means is arranged to digitize the bodily movement signal. A reference voltage used by a comparator 420 is set by signals CS1 and CS2 from an I/O port 408. The comparator 420 compares the reference voltage and the bodily movement signal to convert the bodily movement signal in analog form into a binary digital signal. The digital signal is input to a counter 405 to be obtained as a numeric value. The counter 405, a timer 406, a real-time clock (RTC) 407, the I/O port 408, an input means 409, a central processing unit (CPU) 410, a random-access memory (RAM) 411, a read-only memory (ROM) 412, an LCD driver 413, and a buzzer driver 415 are connected to a bus line. The timer 406 generates interrupt signals in detection cycle Ts and questioning cycle Tm. When an interrupt occurs, the CPU 410 starts processing in accordance with a processing program stored in the ROM 412. In the case of an interrupt in detection cycle Ts, the value of the counter 405 is recorded by being written to the RAM 411. That is, time-sequence data on bodily movements in each detection cycle Ts is stored in the RAM 411. In the case of an interrupt in questioning cycle Tm, the CPU 410 makes the buzzer driver 415 sound a buzzer 416 to notify the wearer of a start of questioning, and also makes the LCD driver 413 successively display on an LCD 414 questions in a question form stored in the RAM 411. The wearer inputs an answer to each question by using the input means 409. Input answers are recorded in the RAM 411. Each time questioning is performed, the CPU 410 reads out time data from the RTC 407 and records it as a questioning execution time in the RAM. The I/O port 408 outputs signals CS1 and CS2 and performs communication with an external PC. All of various set values, questions about health, etc., obtained by communication with the PC are stored in the RAM 411. Conversely, living body information obtained by measurement and questioning results are transmitted to the PC through the I/O port 408.

While the buzzer is used as a notification means in the above-described arrangement, any other type of notification means, e.g., vibration, flashing of the display or a notification lamp, or a symbol mark shown on the display for notification may alternatively be used.

Figure 5:
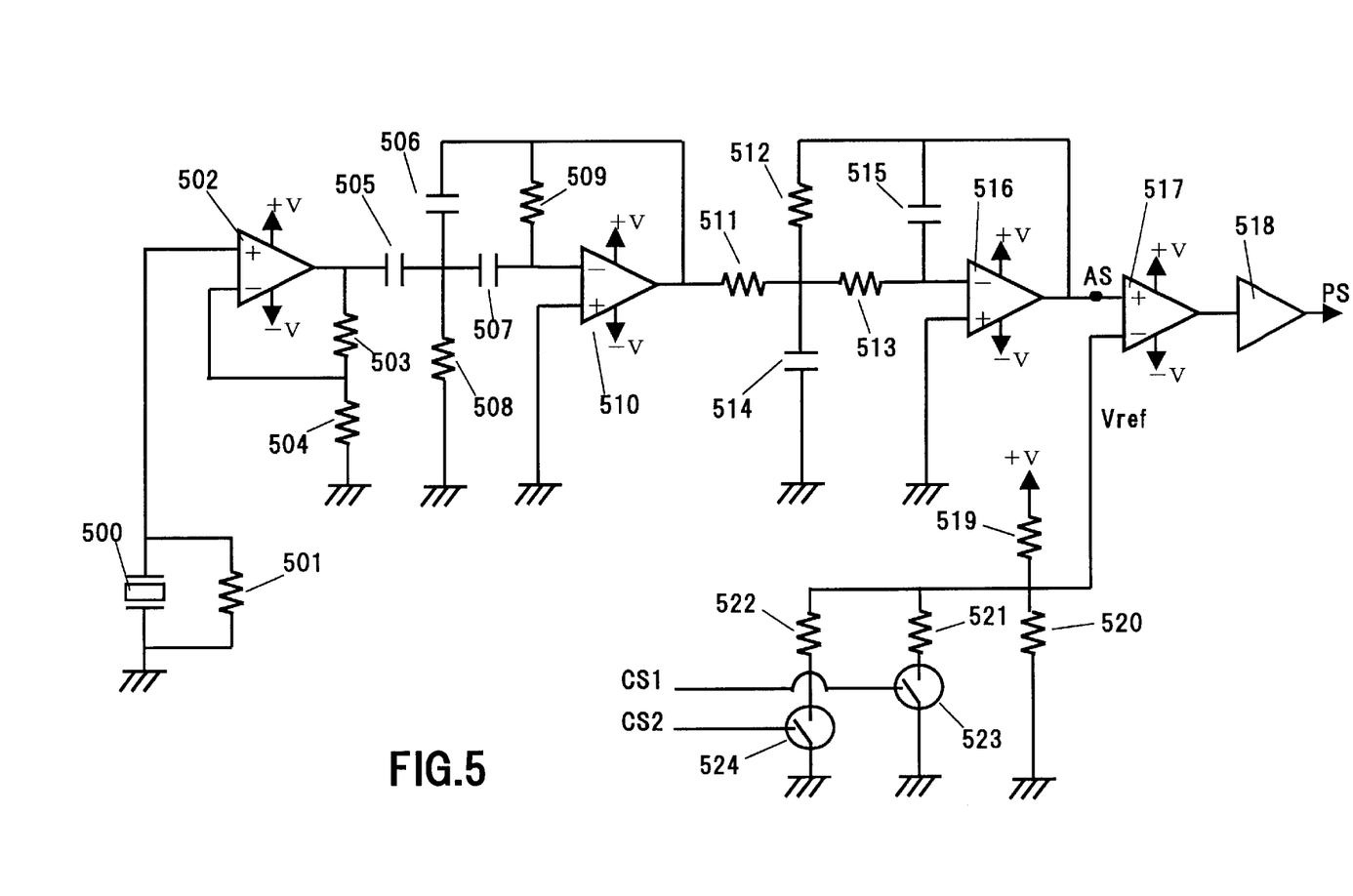
FIG. 5 is a diagram of a bodily movement detection circuit of the portable living body information collector in the embodiment of the present invention.

FIG. 5 shows an example of the bodily movement detection circuit. A piezoelectric-type acceleration sensor 500 is connected in parallel with a resistor 501 and has one electrode grounded and another electrode which is used as an output terminal, and through which a voltage proportional to acceleration is generated. The output terminal is connected to a non-inverting input terminal of an operational amplifier 502. An inverting input terminal of the operational amplifier 502 is connected to an output terminal of the operational amplifier 502 via a feedback resistor 503 and to the ground via a resistor 504. These components constitute an amplifier circuit. The output terminal of the operational amplifier 502 is connected to an inverting input terminal of an operational amplifier 510 via capacitors 505 and 507. An output terminal of the operational amplifier 510, a feedback resistor 509, and a capacitor 506 constitute a feedback circuit. A contact point to which the capacitors 505, 506, and 507 are connected is grounded via a resistor 508. The operational amplifier 510, the capacitors 505, 506, and 507, and the resistors 508 and 509 constitute a multi-feedback-type high-pass filter. The output terminal of the operational amplifier 510 is connected to an inverting input terminal of the next operational amplifier 516 via resistors 511 and 513.

An output terminal of the operational amplifier 516, a feedback resistor 512, and a capacitor 515 constitute a feedback circuit. A contact point to which the resistors 511, 512, and 513 are connected is grounded via a capacitor 514. The operational amplifier 516, the resistors 511, 512, and 513, and the capacitors 514 and 515 constitute a multi-feedback-type low-pass filter. The output terminal of the operational amplifier 516 is connected to a non-inverting input terminal of a comparator 517. A reference voltage Vref is applied to an inverting input terminal of the operational amplifier 517 operating as a comparator. The reference voltage Vref is produced by resistors 519, 520, 521, and 522 and analog switches 523 and 524. The analog switches 523 and 524 are turned on and off by signals CS1 and CS2, respectively, to change the value of reference voltage Vref. It is possible to change the sensitivity of the comparator 517 by changing the reference voltage Vref in this manner. An output from the comparator 517 is formed into rectangular waves of unidirectional half-cycles by a buffer 518. These rectangular waves are input to the counter 405 shown in FIG. 4 to be counted.

Figure 6:
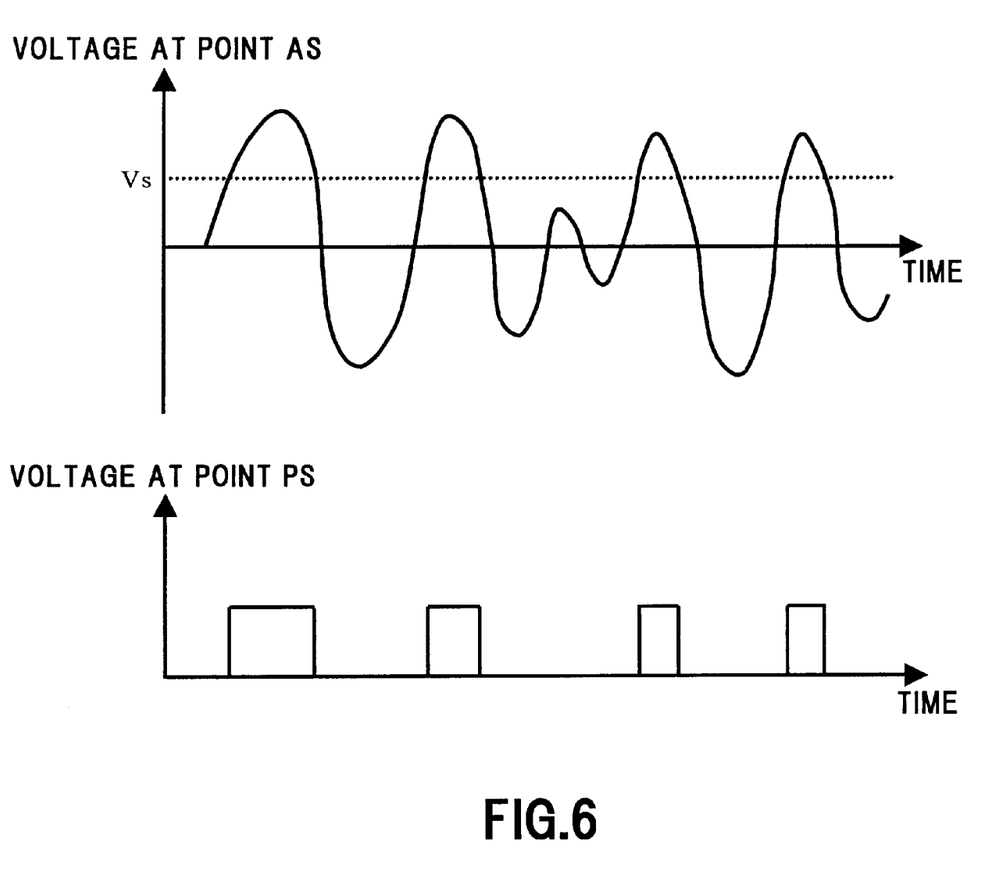
FIG. 6 is a diagram showing a waveform of an output from the bodily movement detection circuit of the portable living body information collector in the embodiment of the present invention.

FIG. 6 shows waveforms at a point AS and an output point PS shown in FIG. 5. Through the point AS, the analog signal representing bodily movements of the wearer is supplied. This signal is compared with the reference voltage Vref by the comparator. The output from the comparator is shaped by the buffer so that the waveform at the point PS is a binary rectangular waveform.

Figure 7:
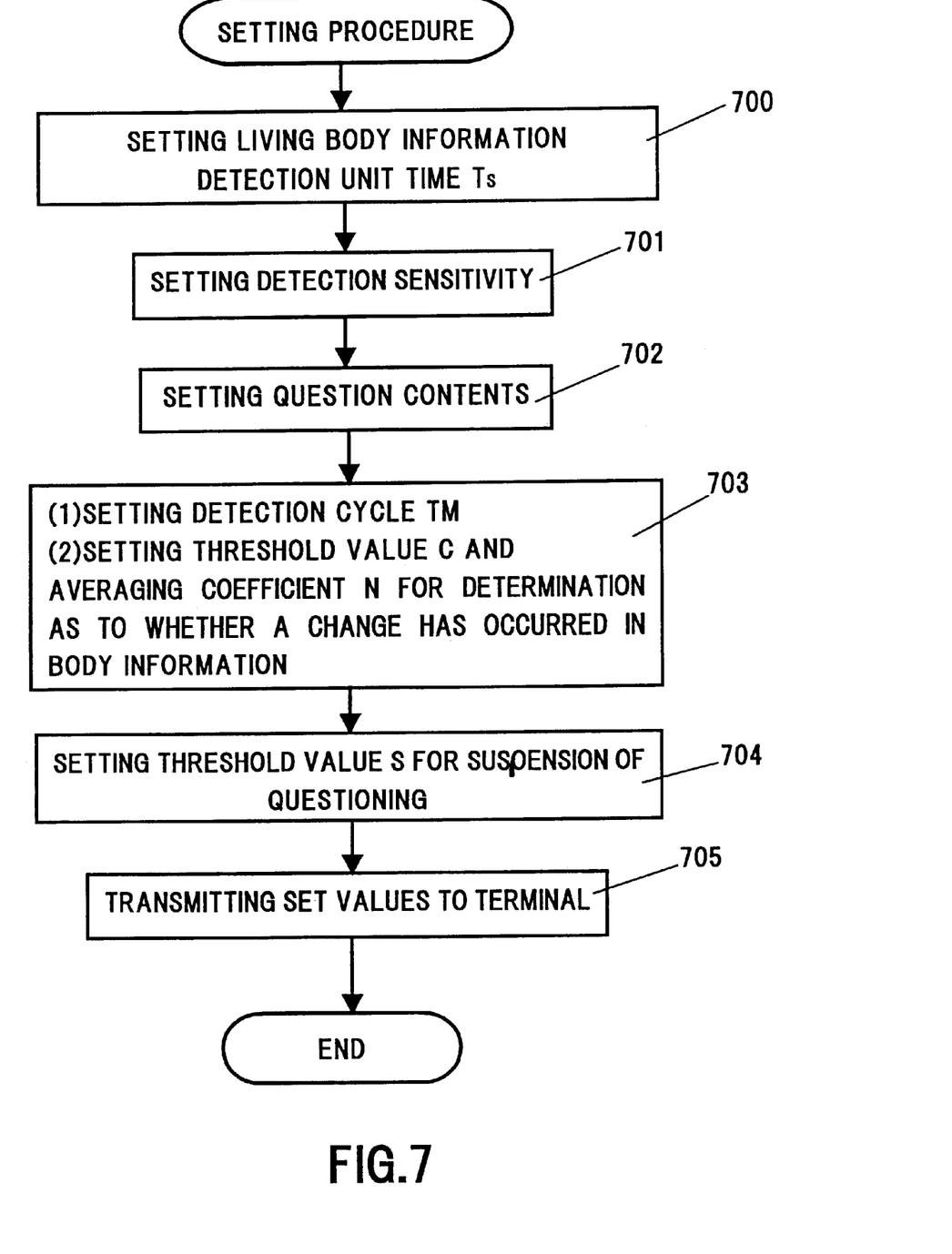
FIG. 7 is a flowchart of a procedure for setting in the portable living body information collector in the embodiment of the present invention.

A procedure for setting of each set value will next be described. FIG. 7 is a flowchart showing a setting procedure. Setting is performed in the state of being connected to a PC as shown in FIG. 2. Set values are determined on the PC and are finally transmitted to the terminal. In step 700, a living body information detection unit time Ts is set. That is, a minimum unit time during which bodily movements of the wearer are detected is determined. The CPU records the counter value in a cycle of time Ts in the RAM. If the time Ts is set to an excessively small value, a considerably large RAM capacity is required. Conversely, if the time Ts is set to an excessively large value, the counter value is leveled, resulting in failure to detect changes of bodily movements. It is preferable to set the time Ts to 5 to 10 minutes. In step 701, a detection sensitivity is set. That is, a reference voltage used by the comparator 517 shown in FIG. 5 is set by setting outputs CS1 and CS2. Generally, a person becomes slower in action as he or she ages. If bodily movements are slower, the amplitude of the signal representing the bodily movements is smaller. In such a case, the detection sensitivity is adjusted to a level suitable for detection of the actual signal. In step 702, questions about health, e.g., "How are you feeling?" and "Are you irritated?" are set. Needless to say, a plurality of candidate questions to be asked may be prepared in advance and a program on the PC may be formed so as to enable selection from the prepared questions, thereby facilitating question setting. Next, in step 703, a questioning cycle is set. A time Tm of several hours is set to determine a cycle in which questioning about health is performed. A threshold value C is set separately from the cycle Tm. With this setting, questioning can be started when a change occurs in living body information exceeding the threshold value C. However, there is a possibility of the amount of bodily movement decreasing temporarily due to a comparatively short length of detection unit time Ts. To avoid such an accidental event, an averaging coefficient N is determined. To calculate a change in living body information, the average of the latter half of 2N number of bodily movement data items in time series lately obtained and the average of the former half of the 2N number of data items are compared with each other. Thus, the average values are compared to absorb a temporary change. In step 704, a threshold value S is set to enable suspension of questioning about health. Questioning during a sleep is avoided by setting the threshold value S. Questioning is normally repeated in the cycle Tm and there is a possibility of arrival of a questioning time in a sleep. However, since bodily movements during a sleep are extremely small, the counter value is compared with the threshold value and a sleeping state of the wearer is recognized to inhibit questioning if the counter value is smaller than the threshold value. The above-described various settings may be made in any order other than the described one. Finally, in step 705, the set values are transmitted to the portable living body information collector, thereby completing the setting procedure. Thereafter, the wearer fit the portable living body information collector around the wrist and starts measurement by performing a key operation. Questioning about health may be initially performed at the start of measurement.

Figure 8:
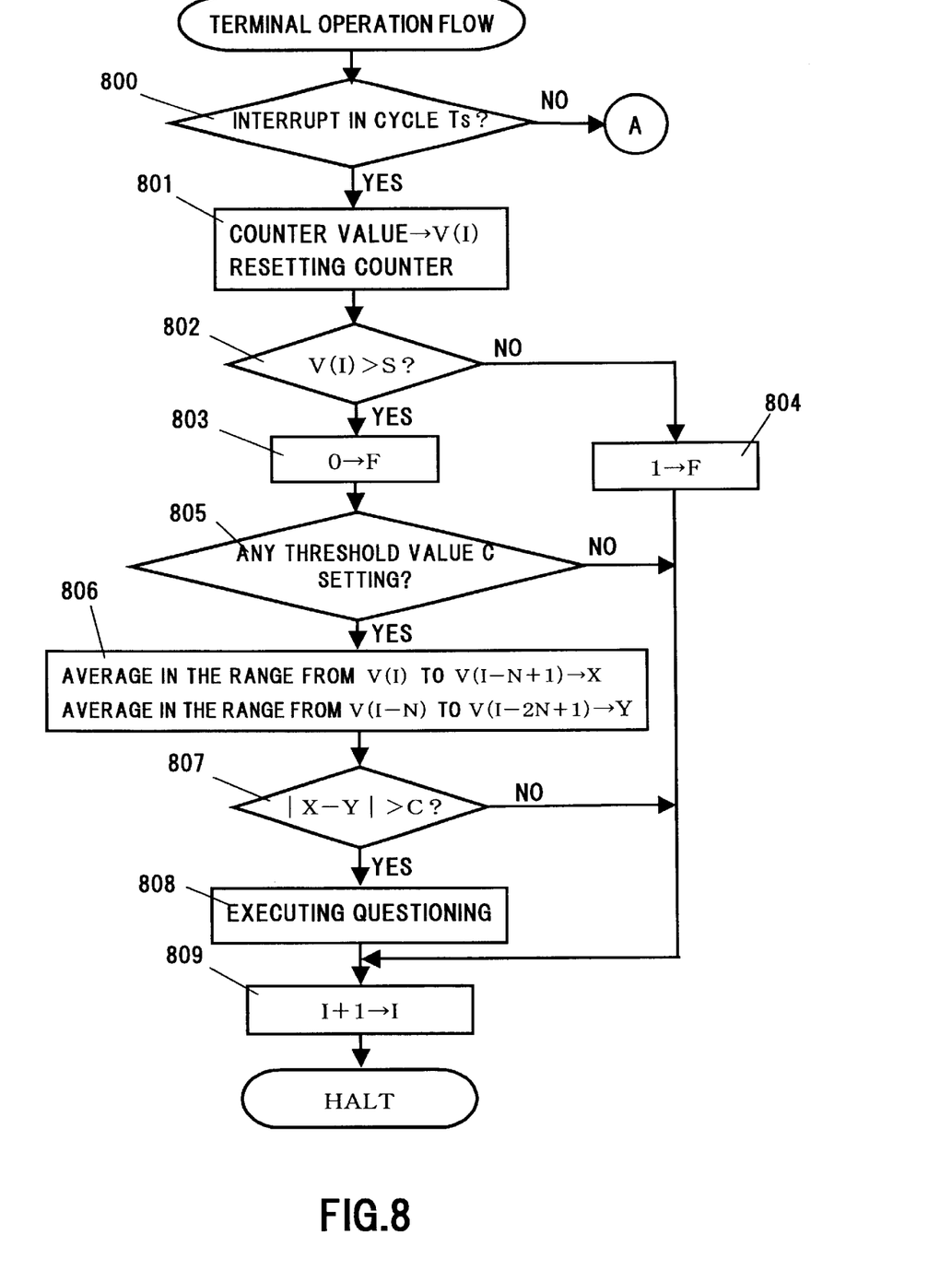
FIG. 8 is a flowchart of the operation of the portable living body information collector in the embodiment of the present invention.
Figure 9:
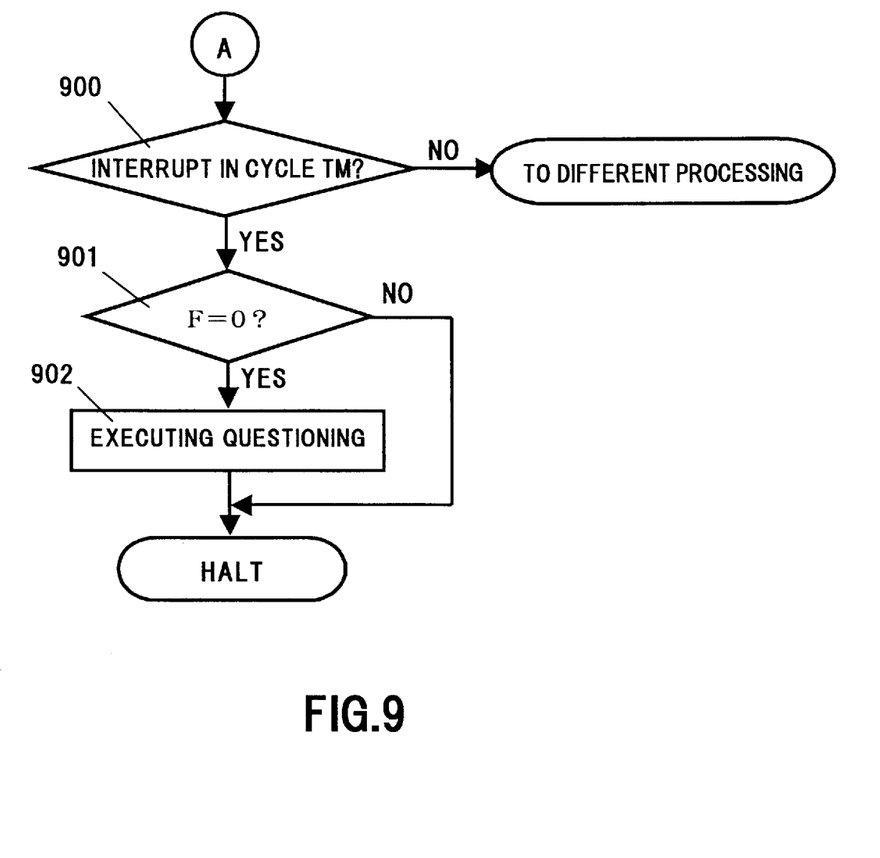
FIG. 9 is another flowchart of the operation of the portable living body information collector in the embodiment of the present invention.

FIGS. 8 and 9 are flowcharts schematically showing the operation of the terminal. When the CPU receives an interrupt, it determines the kind of the interrupt and the process branches according to the result of determination. In this embodiment, a determination is made in step 800 as to whether the interrupt is one in cycle Ts from the timer. In the case of an interrupt in cycle Ts, the process advances to step 801. In other cases, the process moves to step 900 shown in FIG. 9. In step 801, the value of the counter is read to the RAM and the counter is reset. The area of the RAM is assumed to be expressed by an array variable V(I). In step 802, a determination is made as to whether the value V(I) read to the RAM is larger than the threshold value S. If the value V(I) is larger than the threshold value S, it is determined that the wearer is awake, and "0" is written to a flag F in step 803. If the value V(I) is not larger than the threshold value S, "1" is written to the flag F in step 804 and the process moves to step 809. In step 805, a determination is made as to whether the threshold value C has been set. If the threshold value C has been set, the calculation of change in bodily movements is performed in step 806. If the threshold value C has not been set, the process advances to step 809. In step 806, the average in the range from V(I) to V(I−N+1) is represented by X and the average in the range from V(I−N) to V(I−2N+1) is represented by Y. In step 807, a determination is made as to whether the absolute value of the difference between X and Y is larger than the threshold value C. If the absolute value is larger than the threshold value C, questioning is executed in step 808. If the absolute value is not larger than the threshold value C, the process moves to step 809. When the number of counter values recorded in the RAM is smaller than 2N, no average value can be calculated and steps 806, 807, and 808 are not performed (which case is omitted in the flowchart). In step 809, the parameter I of array V is incremented by 1 to prepare for processing with respect to an interrupt in the next cycle Ts.

If it is determined in step 800 that the interrupt is not one in cycle Ts, the process moves to step 900 shown in FIG. 9. In step 900, a determination is made as to whether the interrupt is one in cycle Tm. In the case of an interrupt in cycle Tm, a determination is made in step 901 as to whether the value of the flag F is 0. If F=0, that is, the wearer is awake, then questioning is executed in step 902. If F≠0, it is determined that the wearer is sleeping and the questioning step is skipped. In the case of a different interrupt, e.g., one by a key operation, it is determined in step 900 that the interrupt is one other than that in cycle Tm, and the process advances to a different interrupt processing step.

Figure 10A:
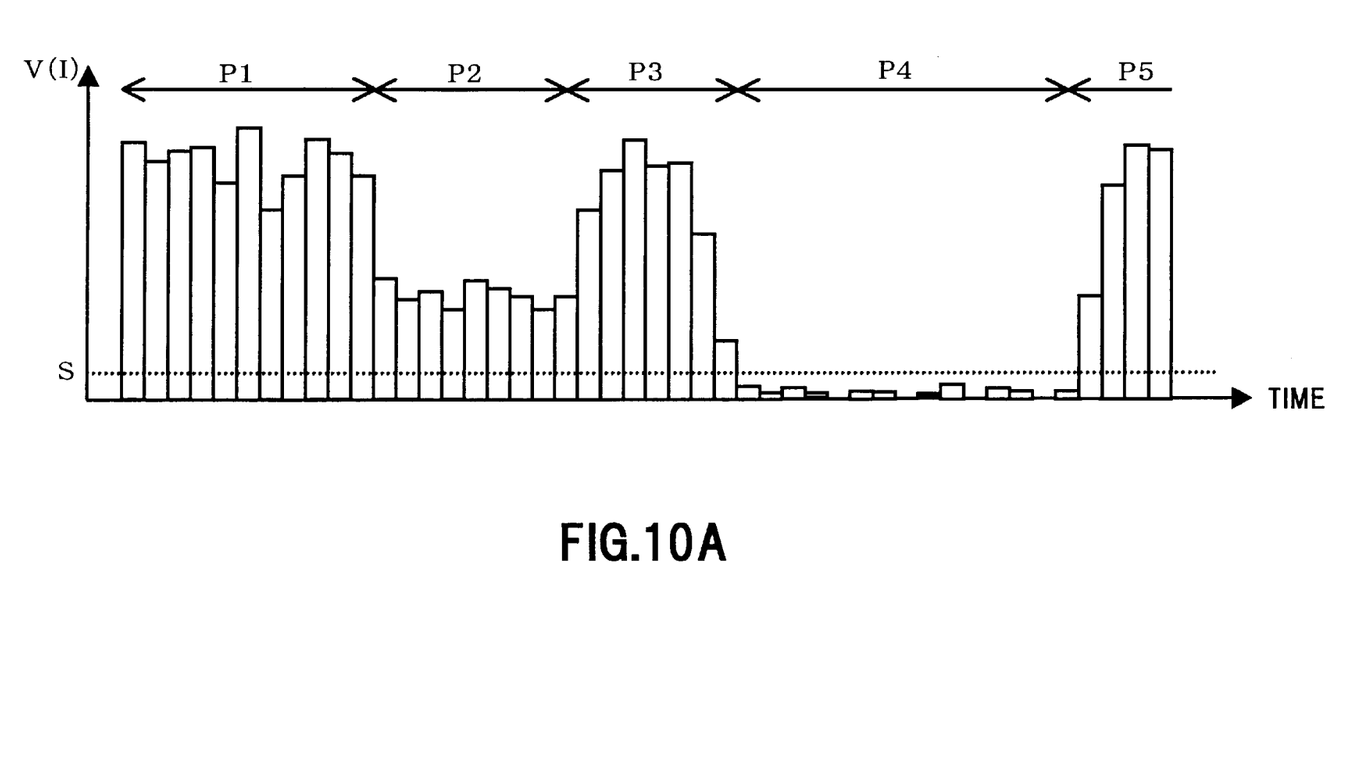
FIGS. 10A and 10B are graphs showing the results of measurement with the portable living body information collector in the embodiment of the present invention.
Figure 10B:
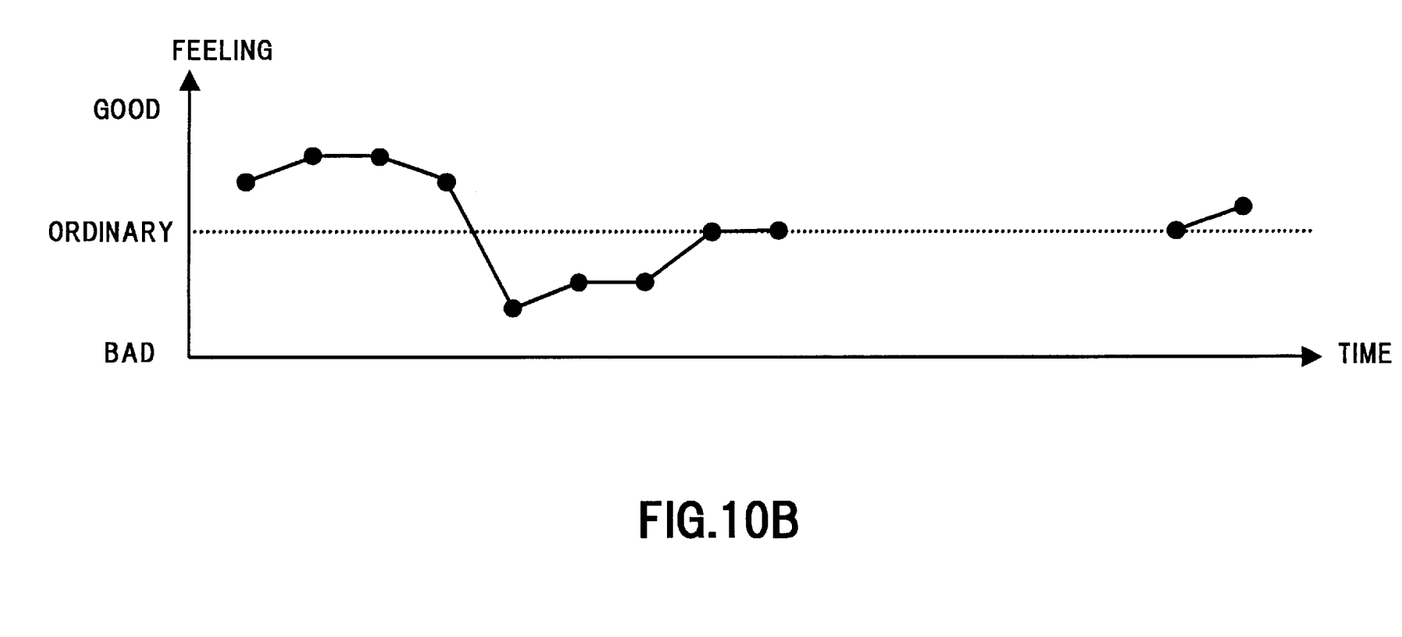

FIGS. 10A and 10B are diagrams showing examples of graphs obtained by reading measurement results to the PC after the measurement and by drawing by a result analysis function. In the graph of FIG. 10A, the abscissa represents time and the ordinate represents bodily movements, i.e., the counter value. In the graph of FIG. 10B, answers to one question about health are also entered with respect to time. The abscissa represents time on the same scale as that in FIG. 10A and the ordinate represents different feelings. The graphs show that the wearer had an increased amount of activity and a good feeling in a period P1, and a reduced amount of activity and a bad feeling in a period P2, that the amount of activity was again increased in a period P3, and that the wearer was asleep during a period P4. Since the counter value during a sleep is smaller than the threshold value S, questioning is skipped during the sleep and no questioning data exists. The wearer woke and became active again in a period P5. Thus, according to the present invention, the activity and the mental condition of the wearer can be recorded over a long period of time as the memory allows, and a record obtained in the above-described manner can be used for psychiatric treatment.

According to the present invention, as described above, information about the living body of a wearer in his or her daily life can be continuously measured in time sequence and the mental condition of the wearer can also be collected in time sequence by asking the wearer some questions. Data obtained in the above-described manner can be used for diagnosis and treatment of melancholy, somnipathy, chronic fatigue syndrome, functional diseases such as irritable bowel syndrome and multiple chemical sensitivity syndrome relating to stress, psychosomatic diseases such as attention deficit hyperactivity disorders, and insanities.

What is claimed is:

1. A wrist-wearable monitoring device comprising: a detecting circuit for detecting a physiological state of a user and outputting a corresponding signal; a memory for storing the output signal of the detecting circuit and at least one question and an answer to the question; a display unit for displaying the question; an input unit for allowing manual input of an answer to the displayed question by the user; a control circuit for controlling the detecting circuit to detect the physiological state at predetermined time intervals, controlling the display unit to display the question at predetermined time intervals, and controlling the memory to store manually input answers to the question sequentially with respect to time; a case for accommodating the detecting circuit, the memory, the display unit, the input unit, and the control circuit; and a wrist strap attached to the case for enabling the monitoring device to be worn on the user's wrist.

2. A wrist-wearable monitoring device according to claim 1; wherein the control circuit compares an output signal of the detecting circuit with a predetermined threshold value at a respective predetermined interval, and controls the display unit to display the question at the respective predetermined interval when the output signal is larger than the threshold value.

3. A wrist-wearable monitoring device according to claim 2; wherein the threshold value is set at a level indicating a sleep state of the user, so that the control circuit controls the display unit to display the question only when the user is not asleep.

4. A wrist-wearable monitoring device according to claim 1; wherein the control circuit compares an output signal of the detection circuit with a predetermined threshold value at a respective predetermined interval and controls the display unit not to display the question at the respective predetermined interval when the output signal is smaller than the threshold value.

5. A wrist-wearable monitoring device according to claim 1; wherein the control circuit compares an output signal of the detection circuit with a predetermined threshold value at a respective predetermined interval and controls the display unit not to display the question at the respective predetermined interval when the output signal is smaller than the threshold value.

6. A wrist-wearable monitoring device according to claim 1; wherein the detection circuit comprises an acceleration sensor for detecting movement of the user.

7. A wrist-wearable monitoring device according to claim 1; further comprising an alarm for notifying the user that the question is being displayed on the display unit.

8. A wrist-wearable monitoring device according to claim 1; wherein the detecting circuit comprises a sensor for sensing the physiological state of the user, a signal processing circuit for amplifying an output signal of the sensor and filtering noise therefrom, and a converting circuit for digitizing an output signal of the signal processing circuit.

9. A wrist-wearable monitoring device according to claim 8; wherein the converting circuit comprises either a quantizing circuit for quantizing the output signal of the signal processing circuit or a numeric converting circuit for converting the output signal of the signal processing circuit into a numeric value.

10. A wrist-wearable monitoring device according to claim 9; wherein the memory stores the result of quantization or numeric conversion performed by the conversion circuit.

11. A wrist-wearable monitoring device according to claim 1; wherein the input unit comprises at least one push-button.

12. A wrist-wearable monitoring device according to claim 1; wherein the input unit comprises a multi-directional switch.

13. A wrist-wearable monitoring device according to claim 12; wherein the question may be answered in any one of a plurality of ways, each of which corresponding to control of the directional switch in a given direction.

14. A wrist-wearable monitoring device according to claim 1; wherein the control circuit includes a time counting circuit for counting time, and controls the display unit to display the time.

15. A wrist-wearable monitoring device according to claim 1; further comprising a communication circuit for establishing communications with an external device.

16. A system comprising: a wrist-wearable monitoring device according to claim 15; and an external device which performs data exchange with the wrist-wearable monitoring device through a communication medium.

17. A system according to claim 16; wherein the external device includes analysis means for analyzing the contents of the memory of the wrist-wearable monitoring device, and a display unit for displaying an analysis result obtained by the analysis means.

18. A wrist-wearable monitoring device according to claim 1; wherein the control circuit determines a first average value of a first plurality of physiological state values sequentially measured by the detecting circuit during a first time period, and a second average value of a second plurality of physiological state values sequentially measured by the detecting circuit during a second time period later in time than the first time period, determines whether a difference between the first average value and the second average value is larger than a predetermined threshold, and controls the display unit to display the question when the difference is larger than the threshold value.

19. A wrist-wearable monitoring device according to claim 18, wherein the total of the first and second pluralities of physiological state values is equal to 2N, wherein N is an integer.

20. A wrist-wearable monitoring device according to claim 19; wherein the first time period immediately precedes the second time period.

* * * * *